(12) United States Patent
Hisanaka

(10) Patent No.: US 6,603,053 B2
(45) Date of Patent: Aug. 5, 2003

(54) SHEET WITH OILY INGREDIENT-CONTAINING LAYER

(75) Inventor: Takayuki Hisanaka, Kagawa (JP)

(73) Assignee: Uni-Charm Corporation, Kawanoe (JP)

( * ) Notice: Subject to any disclaimer, the term of this patent is extended or adjusted under 35 U.S.C. 154(b) by 90 days.

(21) Appl. No.: 09/851,862

(22) Filed: May 9, 2001

(65) Prior Publication Data

US 2001/0041878 A1 Nov. 15, 2001

(30) Foreign Application Priority Data

May 10, 2000 (JP) ........................................ 2000-136724

(51) Int. Cl.⁷ ................................................ A61F 13/15
(52) U.S. Cl. ................................... 604/367; 604/385.28
(58) Field of Search ................................ 604/359, 360, 604/364, 385.28, 367

(56) References Cited

U.S. PATENT DOCUMENTS

| | | | |
|---|---|---|---|
| 5,106,625 A | 4/1992 | Yamamoto et al. | 424/401 |
| 5,919,398 A * | 7/1999 | Nakamura et al. | 424/401 |
| 6,166,285 A * | 12/2000 | Schulte et al. | 424/402 |
| 6,440,437 B1 * | 8/2002 | Krzysik et al. | 424/400 |

FOREIGN PATENT DOCUMENTS

| | | | |
|---|---|---|---|
| JP | 02124813 | 5/1990 | |
| JP | 10-509895 | 9/1998 | ............ A61F/13/54 |
| JP | 10-509896 | 9/1999 | ............ A61F/13/54 |
| JP | 11-510082 | 9/1999 | ............ A61F/13/54 |
| JP | 11-510416 | 9/1999 | ............ A61F/13/54 |
| WO | WO 96/16581 | 6/1996 | ............ A61L/15/26 |
| WO | WO 96/16682 | 6/1996 | ............ A61L/15/34 |
| WO | WO 97/05908 | 2/1997 | ............ A61L/15/10 |
| WO | WO 97/05909 | 2/1997 | ............ A61L/15/10 |
| WO | WO99/22684 | 5/1999 | |
| WO | WO00/64408 | 11/2000 | |

OTHER PUBLICATIONS

European Search Report.

* cited by examiner

*Primary Examiner*—Weilum Lo
*Assistant Examiner*—Jamisue A Webb
(74) *Attorney, Agent, or Firm*—Darby & Darby

(57) ABSTRACT

Provided is a sheet, of which the surface to be in contact with the skin of a wearer has a mixture layer. The mixture layer includes (a) an oily ingredient which is liquid or semi-solid at 25° C., and (b) an ester compound of dextrin with a fatty acid.

16 Claims, 4 Drawing Sheets

SHEET WITH OILY INGREDIENT-CONTAINING LAYER

BACKGROUND OF THE INVENTION

1. Field of the Invention

The present invention relates generally to a sheet capable of transferring a skin-protective oily ingredient to the skin of users. More precisely, the invention relates to such a sheet for absorbent articles including, for example, disposable diapers, sanitary napkins, pantiliners, incontinence pads, etc., and also for wound-protective sheets, skin-care wipers, etc.

2. Description of the Related Art

Recently, various absorbent articles of absorbing excretions are used these days, including, for example, disposable diapers, sanitary napkins, pantiliners, incontinence pads, etc. While worn, such absorbent articles are wetted by wearer's excretions such as sweat, urine, feces, menses and other vaginal discharges, etc., and will often give a stuffy feel to the wearer and irritate the skin of the wearer (i.e., diaper rash and the like). In particular, in the private parts and therearound that are to be in direct contact with excretions, and also in the area to be in direct contact with an elastic member of an absorbent article, for example, in the waist and therearound and also in the thighs and therearound for the diapers, the problem is serious. Lotion or cream that contains a skin-protective ingredient is often applied to the skin of a wearer in order to prevent the wearer's skin from being stuffed and irritated by such a wetted absorbent article. However, this is still problematic in that such lotion or cream soils the hand and using it is troublesome. In particular, babies and aged persons who could not apply it to their own skin by themselves need caregivers' aid, which, however, is troublesome.

To solve the problems as above, Japanese Unexamined Patent Publication (Kohyo) Nos. 10-509895 and 10-509896 disclose a diaper of which a top sheet is coated with a lotion composition. This lotion composition comprises a mixture of a skin-protective emollient and an immobilizing agent to be mobilized at a predetermined temperature. Japanese Unexamined Patent Publication (Kohyo) Nos. 11-510082 and 11-510416 disclose a diaper coated with a mixture that comprises an emollient and an immobilizing agent for immobilizing the emollient.

In these, however, the immobilizing agent will be mobilized at such a predetermined temperature even during storage or transportation of the diapers, and, as a result, the necessary emollient will flow away before use. If so, the amount of the emollient to be effective while the diaper is actually worn will be reduced.

On the other hand, sheets for protecting wounded part such as Band-Aid (registered trademark) are widely used, which are directly applied to the skin with wounded part. However, the sheets of the type are only for protecting the wounded part from physical stimulation without taking account of skin care.

Skin-care sheets applied to the skin in normal condition have also been developed. For spreading an oily ingredient on the skin to form an oily film thereon, it is desirable that the oily ingredient is liquid or semi-solid. However, when a liquid or semi-solid oily ingredient is applied to a sheet, the ingredient will move before or while the sheet comes into contact with the skin, and will fail to form the oily film on the intended part of the skin.

SUMMARY OF THE INVENTION

An object of the present invention is to provide a sheet capable of transferring a skin-protective oily ingredient to the skin of users.

According to an aspect of the invention, a sheet, of which the surface to be in contact with the skin of a wearer has a mixture layer, the mixture layer may comprise;

(a) an oily ingredient which is liquid or semi-solid at 25° C., and (b) an ester compound of dextrin with a fatty acid.

In the sheet of the invention, the skin-protective oily ingredient is fixed on the sheet by the ester compound of dextrin with a fatty acid (i.e., dextrin fatty acid) therein. While in use, the layer of the mixture of the oily ingredient and the ester compound is kept in contact with the skin, so that the oily ingredient is transferred to the skin. Since the oily ingredient is liquid or semi-solid at room temperature, it rapidly spreads on the skin to form an oily film thereon, and the skin is protected by the oily film.

Preferably, the fatty acid for (b) has from 12 to 22 carbon atoms.

Also preferably, the mixture layer contains from 30 to 98% by weight of the oily ingredient and from 70 to 2% by weight of the ester compound.

Also preferably, the ester compound for (b) is dextrin palmitate.

The sheet may be a non-woven fabric.

According to another aspect of the invention, a sheet may be for a liquid-pervious top sheet of an absorbent article, the absorbent article further including a back sheet and an absorbent core sandwiched between the top sheet and the back sheet, the sheet, of which the surface to be in contact with the skin of a wearer has a mixture layer, the mixture layer may comprise;

(a) an oily ingredient which is liquid or semi-solid at 25° C., and (b) an ester compound of dextrin with a fatty acid.

According to still another aspect of the invention, a sheet may be for a leak-preventing cuff for preventing side leakage and/or a leg cuff for preventing leakage around the thighs of a wearer of an absorbent article, the absorbent article further including a liquid-pervious top sheet, a back sheet, and an absorbent core sandwiched between the top sheet and the back sheet, the sheet, of which the surface to be in contact with the skin of a wearer has a mixture layer, the mixture layer may comprise;

(a) an oily ingredient which is liquid or semi-solid at 25° C., and (b) an ester compound of dextrin with a fatty acid.

The sheet may be used for protecting wounds.

The sheet may serve also as skin-care wipers.

DESCRIPTION OF THE PREFERRED EMBODIMENTS

Figure 1:
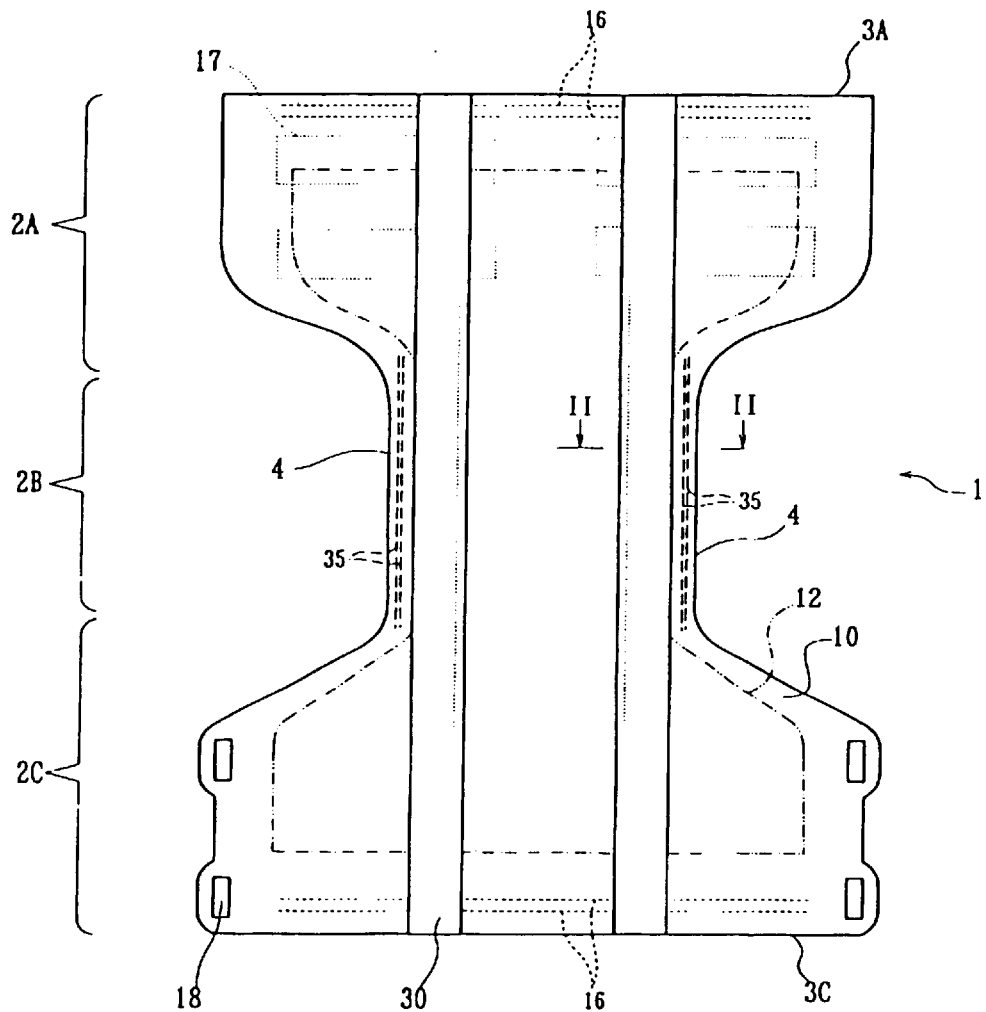
FIG. 1 is a plan view of a diaper for one embodiment of the invention, with its liquid-receiving side being in front. In the diaper, the top sheet is made of a sheet of the invention that has an oily ingredient-containing layer.
Figure 2:
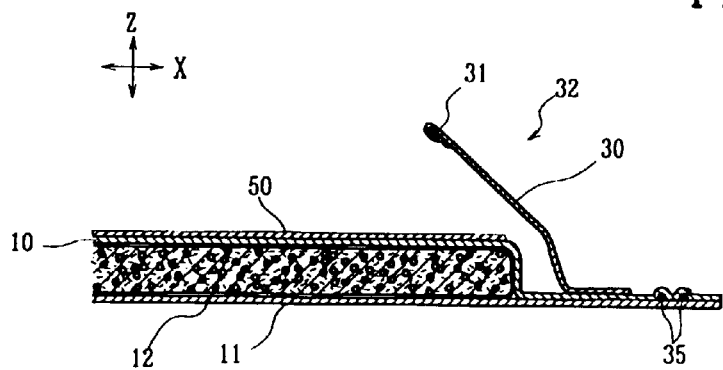
FIG. 2 is a cross-sectional view of the diaper of FIG. 1, cut along the line II—II.

For one embodiment of the invention, a disposable diaper as a type of absorbent article is described with reference to the accompanying drawings. This is provided with a sheet that has an oily ingredient-containing layer of the invention. FIG. 1 is a plan view of the diaper, with its liquid-receiving side being in front. In this, the top sheet is made of the sheet of the invention that has the oily ingredient-containing layer. FIG. 2 is a cross-sectional view of the diaper of FIG. 1, cut along the line II—II.

As shown in FIG. 1, a disposable diaper 1 of the invention is a hour-glass shaped, open type diaper. The disposable diaper is composed of a front area 2A to be fitted to the abdominal region of the wearer, a back area 2C to be fitted to the buttocks and/or the back thereof, and a center area 2B to be fitted to the crotch thereof. In this, the direction extending from the front area to the back area via the crotch area is designated by Y (this is a longitudinal direction of the diaper); and the direction perpendicular to the direction Y is designated by X (this is a transverse direction of the diaper). As shown in FIG. 2, the direction extending toward the wearer is designated by Z.

The disposable diaper 1 comprises a liquid-pervious top sheet 10 to be faced the skin of the wearer, a liquid-impervious back sheet 11 to be faced an external support such as an underwear (opposite the top sheet 10), and an absorbent core 12 sandwiched between the top sheet 10 and the back sheet 11. All these top sheet 10, back sheet 11 and absorbent core 12 are in the form of a hour-glass, respectively. Around the absorbent core 12 between them, the top sheet 10 and the back sheet 11 are bonded to each other with a hot-melt adhesive and the like.

When the diaper 1 is worn, back flaps protruding from the back area 2C in the direction X are respectively laid on the back sheet 11 in the front area 2A, and fastener sheets 18 provided on both side edge portions of the top sheet 10 in the back flaps of the back area 2C are fastened with fastener portions 17 provided on the back sheet 11 in the front flaps protruding from the front area 2A in the direction X, around the waist of the wearer. While the diaper 1 is thus worn, elastic members 16 provided around a waist portion of the diaper elastically expand and contract, and, as a result, the diaper 1 is well fitted to the body of the wearer around the waist thereof.

The diaper 1 of the invention is provided with liquid-impervious strip sheets 30 in vicinity of both longitudinal side edges 4 of the top sheet 10; and one side edge of each strip sheet 30 adjacent to the center of the diaper 1 (i.e., a free end of the strip sheet 30) is provided with an elastic member 31. The other side edge of each strip sheet 30 and the remaining two opposite end edges thereof are all bonded to an upper surface of the top sheet 10 to form a pair of leak-preventing cuffs 32. While the diaper 1 is worn, the free end of each cuff 32 adjacent to the center of the diaper 1 rises up to prevent side leakage, and the upper side in the direction Z of each leak-preventing cuff 32 is kept in contact with the skin of the wearer.

In the region of both side edges 4, 4 in the direction X of the diaper 1 (i.e., longitudinal side edges) in which the absorbent core 12 does not exist (this is outside the absorbent region of the diaper 1), elastic members 35 are bonded and fixed to the diaper 1 between the top sheet 10 and the back sheet 11, extending in the direction Y of the diaper 1. The elastic members 35 elastically expand and contract in the direction Y, whereby the top sheet 10 and the back sheet 11 are elastically expanded and contracted on both side edges 4, 4 in the direction X of the diaper 1. While the diaper 1 is worn, the elastic members 35 thus form a pair of leg cuffs that are kept in contact with the thighs of the wearer.

In the region of the disposable diaper 1 of the invention where the absorbent core 12 exists, a mixture layer 50 that contains at least the following two ingredients (a), (b) is provided on the surface of the top sheet 10 that receives the excretions discharged by the wearer (this surface is also referred to as a body facing surface).

(a) an oily ingredient which is liquid or semi-solid (for example, waxy) at 25° C., and (b) an ester compound of dextrin with a fatty acid.

The oily ingredient (a) is a compound that forms an oily film on the uppermost surface of the skin of the wearer so as to protect the wearer's skin from being irritated. The oily film thus formed on the wearer's skin can protect the skin from being irritated by the chemical stimulation caused by excretions and surfactant and by the physical stimulation caused by the contact of the diaper to the skin.

Preferably, the oily ingredient (a) is insoluble in water, in order that the oily film formed by it on the skin does not dissolve in the wearer's sweat and excretions and does not flow away. However, it may be a compound emulsified in water by use of emulsifying agent, when mixed and shaken with water. Also preferably, it may be a fatty acid having a hydrophilic group as an oily ingredient. In case of employing the fatty acid, even if the oily ingredient having a hydrophilic group has widely spread over the surface of the top sheet 10, it will hardly lower the liquid permeability of the top sheet 10. Since the oily film-forming compound is kept in direct contact with the skin of the wearer, it is desirable that the compound is colorless or white, or is at least nearly colorless or whitish.

Concrete examples of the oily ingredient (a) are mentioned below, which, however, are not limitative. Needless to say, any other compounds not mentioned below are employable herein, so far as they have the ability to form an oily film. One or more of the compounds mentioned below may be used herein either singly or as combined.

(1) Vegetable Based Oils

Drying oils such as grape seed oil, safflower oil, soybean oil, etc.; semi-drying oils such as sesame oil, corn oil, cotton seed oil, rape seed oil, sunflower oil, etc.; non-drying oils such as avocado oil, almond oil, olive oil, sasanqua oil, camellia oil, persic oil, castor oil, peanut oil, etc. Among these, preferred are semi-drying oils and non-drying oils in view of their time-dependent stability.

(2) Vegetable Based Fats

Cacao butter, palm oil, palm kernel oil, macadamia nut oil, haze tallow, coconut oil, etc.

(3) Vegetable Based Waxes

Carnauba wax, candelilla wax, jojoba oil, etc.

(4) Animal Based Oils and Fats

Turtle oil, mink oil, egg yolk oil, beef tallow, lard, sardine oil, shark liver oil, herring oil, saury oil, mackerel oil, menhaden oil, etc.

(5) Animal Based Waxes

Whale wax, bees wax, lanolin, etc.

(6) Hydrocarbons

Dialkyl carbonates having 14 or 15 carbon atoms, vaseline, paraffin, squalane, pristane, ozocerite, ceresine, microcrystalline wax, etc.

(7) Derivatives from the Oily Ingredients (1) to (6) Prepared by Hydrogenating the Unsaturated Part of the Compounds Among the oily ingredients mentioned above, preferred are oils and fats generally used in cosmetics as they do not irritate the skin. More preferred are dialkyl carbonates having 14 or 15 carbon atoms, as they are safe and can well spread on the skin. Also preferred is using vegetable based oil such as macadamia nut oil or the like that is soft to the skin, along with dialkyl carbonates having 14 or 15 carbon atoms. In view of its ability to gel that will be described in detail hereinafter, the compound for the oily ingredient preferably has a polar group. However, since the ability of the oily ingredient to gel can be controlled by varying the viscosity thereof or by mixing a plurality of compounds to prepare the oily ingredient, compounds not having a polar group can also be used for the oily ingredient.

The oily ingredient (a) is liquid or semi-solid at room temperature, as it must spread on the skin. Therefore, if only the oily ingredient is applied to the diaper 1, it will penetrate into the constituent members of the diaper 1, or will move through them before or while the diaper 1 is actually worn. If so, the necessary amount of the oily ingredient could not transfer to the skin of the wearer. Therefore, an ester compound (b) of dextrin with a fatty acid is added to the oily ingredient (a), so that the oily ingredient (a) is gelled with the ester compound (b) and is fixed on the surface of the top sheet 10 of the diaper 1.

When the oily ingredient (a) is mixed with the ester compound (b), the resulting mixture forms a gel. The gelled mixture is, when applied to the surface of the top sheet 10, prevented from penetrating through the top sheet 10 to move toward the absorbent core 12, to a high degree of possibility. Therefore, it is possible to surely form the layer 50 on the surface of the top sheet 10. While the diaper 1 is worn, the mixture layer 50 formed on the top sheet 10 is kept in contact with the skin of the wearer, and, as a result, the oily ingredient (a) in the gelled layer 50 melts out and moves toward the skin to thereby form an oily film on the skin. At room temperature, the gelled mixture layer 50 does not move with ease, and only when kept in contact with the skin of the wearer, it surely forms the oily film in the intended area. In addition, the sheet of the invention does not require any excessive amount of the oily ingredient to lower the cost of production.

In the ester compound (b), dextrin forms an ester bond with a fatty acid. In this, the fatty acid having a larger number of carbon atoms produces a mixture of (a) and (b) having a higher degree of gel strength. Therefore, in the invention, it is desirable that the fatty acid has from 12 to 22 carbon atoms. If the number of carbon atoms that constitute the fatty acid is lower than the lowermost limit of the defined range, the gel strength of the mixture will be low. In this case, the layer 50 of the mixture will penetrate through the top sheet 10 to move on the side of the absorbent core 12, and, as a result, the absorbability of the absorbent core 12 in the diaper 1 will be degraded and the necessary amount of the oily ingredient could not transfer to the skin of the wearer. On the other hand, if the number of carbon atoms that constitute the fatty acid is over the uppermost limit of the defined range, the gel strength of the mixture will be too high. In this case, the oily component could hardly transfer to the skin, and the mixture layer 50 will be hard to give an uncomfortable feeling to the wearer. Fatty acids having a larger number of carbon atoms have a higher melting point. Therefore, if the number of carbon atoms that constitute the fatty acid for use herein is over the uppermost limit of the defined range, the mixture must be heated at high temperature when its layer 50 is formed, and the ester compound in the mixture will be denatured at such high temperature. In addition,when the mixture layer 50 heated at high temperature is formed on the top sheet 10, the feel of the top sheet 10 will be degraded.

Preferred examples of the ester compound (b) are dextrin palmitate, dextrin stearate, dextrin behenate, dextrin myristate, cocoyl dextrin, dextrin laurate and others in which the fatty acid has from 12 to 22 carbon atoms. Among these, more preferred are safe ones that are usable in cosmetics. Even more preferred is dextrin palmitate, as being colorless (or white) and safe.

With the mixture of (a) and (b), preferably, the oily ingredient (a) accounts for from 30 to 98% by weight and the ester compound (b) accounts for from 70 to 2% by weight (i.e., the ratio of the oily ingredient (a) to the ester compound (b) falls between 30:70 and 98:2), in order that the oily ingredient (a) can surely form the oily film on the skin of the wearer and can be well gelled to be fixed on the diaper 1. More preferably, the oily ingredient (a) accounts for from 70 to 95% by weight, and the ester compound (b) accounts for from 30 to 5% by weight (i.e., the ratio of the oily ingredient (a) to the ester compound (b) falls between 70:30 and 95:5).

In the mixture layer 50, the ester compound of dextrin with a fatty acid (b) is existed in a gel network. In the disposable diaper 1 before use, the oily ingredient (a) which is liquid or semi-solid, is enclosed in this gel network. Namely, the ester compound (b) having a gel structure is placed into a swollen condition by the oily ingredient (a).

When the disposable diaper 1 is fitted to the wearer and the mixture layer 50 applied to the top sheet 10 is contact with the wearer's skin, an external force such as body pressure and frictional force is applied to the mixture layer 50. Due to this external force, the gel structure of the ester compound (b) is destroyed, and the oily ingredient (a) enclosed therein is released to be transferred to the wearer's skin.

In the invention, since the oily ingredient (a) is held in the gel structure of the ester compound (b), it is possible to significantly reduce the amount of the oily ingredient (a) to be transferred to the absorbent core 12. On the other hand, upon manufacture, transportation or storage, it is possible to surely prevent the oily ingredient from flowing away before use.

Further, the present invention has a mechanism such that the gel structure of the ester compound (b) is destroyed by the external force, and the oily ingredient (a) is released to be transferred to the wearer's skin. Accordingly, the oil ingredient in the mixture layer 50 can be efficiently transferred to the wearer's skin.

Still further, even after the gel structure is destroyed, the estor compound (b) remains on the top sheet 10, and only the oily ingredient (a) is transferred to the wearer's skin. In other words, since only the oily ingredient (a) can be selectively transferred to the wearer's skin, it is possible to reduce the amount of the oily ingredient (a) necessary to impart the desired protective benefit.

Among the preferred examples of the ester compounds set forth above, dextrin palmitate has a superior deposit efficiency of the oily ingredient (a).

Furthermore, when dextrin palmitate is used as the ester compound (b), dextrin palmitate can make a fine crystal on the top sheet 10 to improve lubricity and tactile impression.

Figure 7:
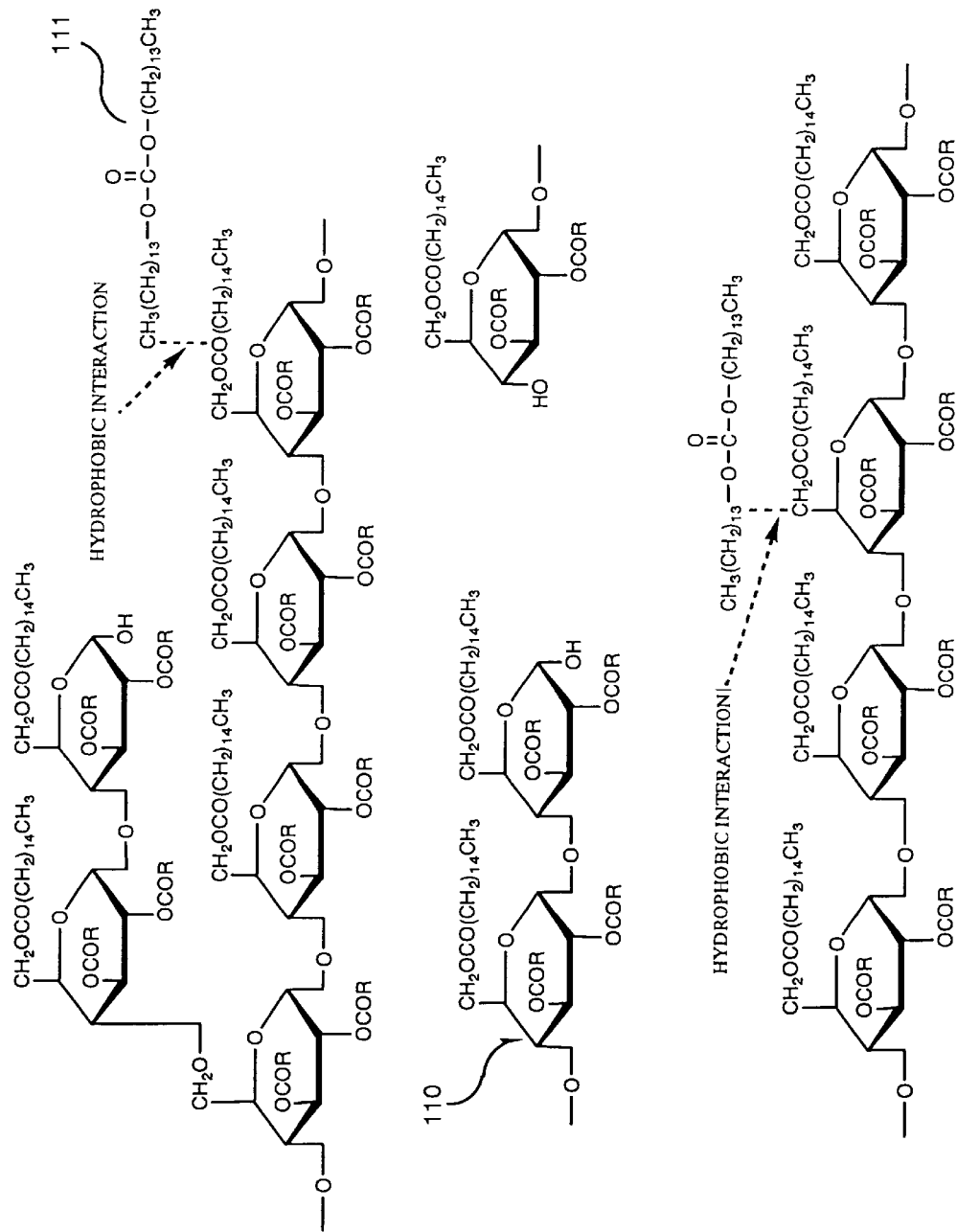
FIG. 7 is a structural formula of dextrin palmitate for one example of the ester compound (b) according to the present invention.

FIG. 7 is a structural formula of dextrin palmitate for one example of the ester compound (b) according to the present invention.

As shown in FIG. 7, dextrin palmitate is included in polysaccharide in which glucoside bonding is effected. Namely, glucose 110 in which hydroxyl group is esterified with palmitic acid, is bonded by α1→4 glucoside bonding or α1→6 glucoside bonding. In FIG. 7, two-position and three-position acyl groups are respectively represented by COR, and COR=$CO(CH_2)_{14}CH_3$.

As shown in FIG. 7, dextrin palmitate having polysaccharide chain structure agglutinates into a network by hydrogen bonding between polysaccharide chains or hydrophobic interaction to make a gel structure.

The oil ingredient (a) such as dialkyl carbonates 111 is held within the gel structure due to hydrophobic interaction around acyl group of dextrin palmitate.

Since the mixture of (a) and (b) is kept in direct contact with the skin of the wearer, it is necessary not to irritate the skin. For example, the human skin in healthy condition generally has a pH of from 4.5 to 7.5. Accordingly, it is desirable that the mixture layer has a pH of from 4.5 to 7.5, more preferably from 5.0 to 7.0. In addition, since the mixture will adhere to the skin of the wearer, it is desirable that the mixture is colorless or white, or is nearly colorless or whitish.

The mixture of (a) and (b) may further contain any other skin-protective ingredients. For example, it may contain any of anti-inflammatory ingredients of peony, scutellaria roots, Saint-John's-wort, camomile, peach leaves, loquat leaves, mugwort, perilla extract, etc.; moisturizers of silk fibroin, silk sericin, collagen, seaweed extract, etc.; anti-oxidative (deodorant) ingredients of green tea, bamboo extract, etc.; pH controllers (or those capable of keeping the wearer's skin slightly acidic), such as natural fruits acids (malic acid, succinic acid, citric acid, tartaric acid, lactic acid, etc.), alkali metal salts and alkaline earth metal salts (phosphates, carbonates, etc.), etc. The additional skin-protective ingredients may be formulated and added to the mixture in any desired manner, depending on the condition of the wearer's skin.

The mixture may contain surfactant that enables better penetration of the oily ingredient into the skin. For the surfactant, preferred are sucrose esters with fatty acids that do not irritate the skin.

The mixture layer 50 may be formed by applying a predetermined amount of the mixture onto the top sheet 10 (substrate). For example, the mixture may be applied thereto by printing, such as gravure printing or flexographic printing. As the case may be, a coating technique for thermal adhesives (e.g., a hot-melt adhesive and the like) is also employable. Concretely, the mixture to form the layer is melted by use of a hot-melt applicator, and then (1) a predetermined amount of the resulting melt is extruded out by use of a gear pump, and is directly coated on the substrate via a die kept in contact with the substrate by use of a slot coater; or (2) the melt is extruded out through a die, and then sprayed over the substrate under air pressure; or (3) the melt is fiber-wise extruded out through a die, and directly bonded to the substrate. Still employable herein is a dyeing technique. Concretely, the substrate is directly dipped in a coating liquid of the mixture to form the layer, and then the excess coating liquid is squeezed out of the substrate (this is referred to as dipping).

Figure 3A:
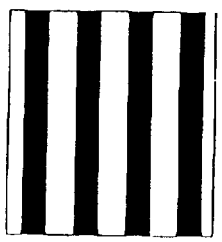
FIGS. 3A, 3B and 3C are plan views of different patterns of the oily ingredient-containing layer of the sheet of the invention.
Figure 3B:
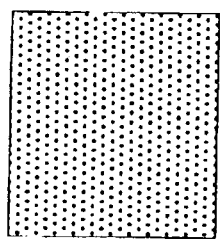
Figure 3C:
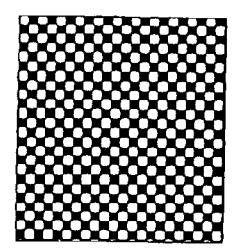

In order to ensure the maximum coating result with a minimum coating amount of the mixture to form the intended layer, it is desirable that the coating mixture is applied to the uppermost fibrous region of the substrate. To that effect, the printing technique (gravure printing or flexographic printing), as well as the coating technique for thermal adhesives are preferred herein among the techniques set forth above. Regarding the coating pattern of the layer 50 thereon, the substrate may be uniformly coated with the layer on its entire surface as in FIG. 2. As the case may be, the layer may have a stripe pattern as shown in FIG. 3A, or a dot pattern (a polka-dot pattern) as shown in FIG. 3B, or a lattice pattern as shown in FIG. 3C. Considering the liquid permeability of the top sheet 10 coated with the mixture layer, it is desirable that the area substantially coated with the mixture accounts for from 30 to 70% of the entire area of the top sheet.

Preferably, the amount of the mixture (a) and (b) to be coated on the top sheet 10 falls between 1 and 50 $g/m^2$, more preferably between 1 and 30 $g/m^2$, in order not to detract from the liquid permeability of the top sheet 10.

The top sheet 10 to be coated with the mixture layer 50 may be made of a non-woven fabric having a Metsuke (unit weight) of from 10 to 60 $g/m^2$, for which, for example, usable are polyolefin or polyester synthetic fibers, semi-synthetic fibers of rayon or the like, or natural fibers of pulp, cotton or the like. The fineness of these fibers may fall between 1.1 and 5.5 dtex. For the top sheet 10, especially preferred is a thermally-bonded non-woven fabric having high strength and good workability. Other non-woven fabrics of hydrophilicated hydrophobic fibers or hydrophilic fibers produced in a mode of point bonding, air-through bonding, spun bonding or spun lace bonding are also usable for the top sheet 10. Further usable for it are perforation webs, which may be prepared by forming a sheet of polyethylene (having a density of from 0.86 to 1.1 $g/m^3$) and/or polypropylene (having a density of from 0.89 to 1.2 $g/m^3$) through extrusion either singly or as combined, followed by perforating the sheet with hot air jets or with hot needles to make the sheet have liquid-pervious through-holes (perforations), or by depositing a fiber web on a film followed by perforating the resulting sheet with hot air jets or with hot needles to make the sheet have liquid-pervious through-holes (perforations). Any webs are usable for the top sheet 10, provided that their liquid permeability and absorbability comes up to the standard of JIS L-1092 (testing methods for water resistance of textiles: resistance to water of from 0 to 300 $mmH_2O$ in a test method A (low-pressure method) for the degree of resistance to water), and provided that their air permeability comes up to the standard of JIS L-1906 (testing methods for non-woven fabrics made of filament yarn: air transmission rate of from 5 to 700 $cm^3/cm^2/sec$ in an air permeation test for fragile). In order to ensure the layer formation thereon, the top sheet 10 may have a multi-layered structure (laminate sheet) of which the uppermost layer to be coated shall have the highest density.

The back sheet 11 is pervious to air but not to liquid, and is formed of, for example, a polyolefin resin sheet. On the other hand, non-woven fabric may be used for the back sheet 11, with a water-resistant film being sandwiched between the back sheet and the absorbent core. When it is put on any other absorbent articles, the back sheet 11 may be made of a liquid-pervious sheet.

The absorbent core 12 may be formed of an absorbent material, for example, powdery pulp or its mixture with high-absorbent polymer. For this, powdery pulp or its mixture with high-absorbent polymer may be wrapped with an absorbent sheet of tissue or the like. For example, the fastener portion 17 may be an adhesive tape of rubber or acrylic resin, etc.; and the fastener sheet 18 may be made of a resin film.

In the illustrated embodiment, the mixture layer 50 is present in the entire region of the absorbent core 12, but may not be provided in the entire region thereof. For example, the layer 50 may be provided in the front area 2A which is fitted to the abdominal region of the wearer and/or in the back area 2C which is fitted to the buttocks and/or the back of the wearer, in order to protect the wearer's abdominal region and buttocks from being irritated and in order not to lower the liquid permeability of the top sheet 10. Not limited to these, the layer 50 may be provided in any other region of the diaper 1 that shall be in direct contact with the skin of the wearer.

Figure 4:
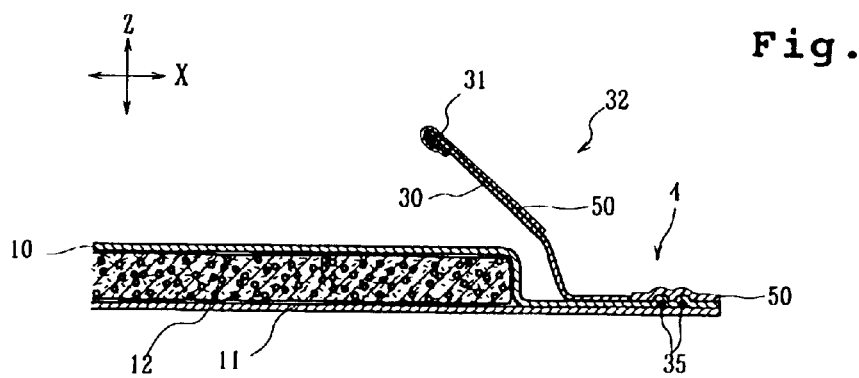
FIG. 4 is a partial-cross-sectional view of the second embodiment of the invention.

FIG. 4 is a partial cross-sectional view of the second embodiment of the invention, and this corresponds to FIG. 2 showing the first embodiment as above. In this embodiment of FIG. 4, the free end side of each leak-preventing cuff 32 (this shall be in direct contact with the skin of the wearer, and is provided with an elastic member 31) is coated with a mixture layer 50. Furthermore, the region adjacent a side edge 4 to form a leg cuff (this shall be in direct contact with the thighs of the wearer, and is provided with an elastic member 35) is coated with the mixture layer 50. In this embodiment, the layer 50 protects the skin around the crotch and the thighs of the wearer from being irritated.

While the wearer is wearing the diaper, the skin being in contact with the elastic members of the diaper is subjected to much physical stimulation as being always rubbed against the elastic members. Therefore, it is desirable that the wearer's skin in that region is specifically protected by some means as in the manner illustrated herein. Apart from the embodiments illustrated herein, the mixture layer 50 may be disposed in the waist part of the diaper provided with the elastic members 16.

The first and second embodiments of the open type diaper have been disclosed herein for the absorbent article having the sheet of the invention. Not limited to these, the invention is applicable to any others such as panty type diapers, incontinence pads, sanitary napkins, pantiliners, etc.

Figure 5:
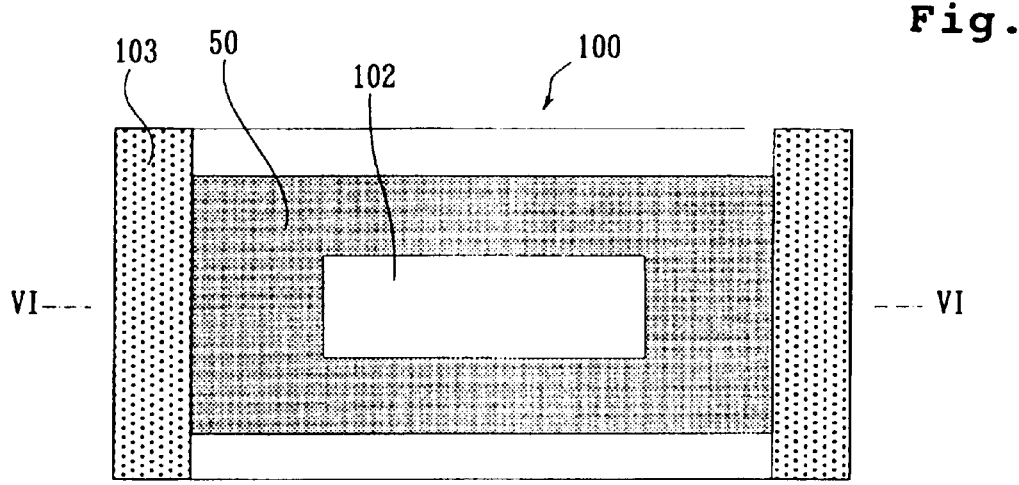
FIG. 5 is a plan view of the third embodiment of the invention.
Figure 6:
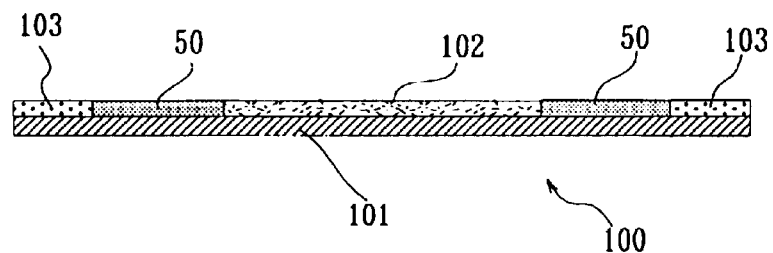
FIG. 6 is a cross-sectional view of FIG. 5, cut along the line VI—VI.

FIG. 5 is a plan view of third embodiment of the invention, in which the sheet of the invention having an oily ingredient-containing layer formed thereon serves to protect wounded part. FIG. 6 is a cross-sectional view of FIG. 5, cut along the line VI—VI. As shown in FIG. 5, a sheet 100 for protecting wounded part is to cover the wounded part of the skin to protect it from being in contact with any others.

The sheet 100 for protecting wounded part comprises a substrate sheet 101 made of a non-woven fabric or the like, a piece of gauze 102 disposed on the substrate sheet 101 in the center portion, a mixture layer 50 of (a) and (b) that surrounds the gauze 102, and an adhesive layer 103 disposed on each side edge portion of the substrate sheet 101. In its use, the sheet 100 is directly applied to the skin so that the gauze 102 is kept in direct contact with the wounded part of the skin, and this is fitted to the skin via the adhesive layer 103. Since the sheet 100 for protecting wounded part is provided with the mixture layer 50, it forms an oily film around the wounded part of the skin while it is attached to the skin. The oily film protects the skin around the wounded part, so that it can minimize the area of the skin that may be irritated by the adhesive layer 103. In the sheet 100, the gelled mixture layer 50 does not move to any other area of the substrate sheet 101, and does not penetrate into the substrate sheet 101, and as a result, it is hardly wasted.

In this embodiment, the mixture layer 50 may be formed also on the surface of the gauze 102, or may be formed only on the surface of the gauze 102.

Apart from the embodiments illustrated herein, the sheet of the invention having an oily ingredient-containing layer formed thereon may also be used for skin-care wipers applied to the skin in normal condition. In this case, for example, a mixture layer 50 is formed on the entire surface of a substrate sheet. In the skin-care wipers of this type, the oily ingredient does not move outside the substrate sheet before use. While in use, even when the wiper is kept vertical to be in contact with the face of a user, the oily ingredient therein does not flow down, and the mixture layer 50 can be surely kept in contact with the skin of the face. In that condition, an oily film is formed on the skin.

By using the sheet of the invention having an oily ingredient-containing layer formed thereon, it is possible to surely have a skin-protective oily ingredient applied to its skin in a simplified manner. This oily ingredient-containing layer hardly moves on the surface of the sheet, and hardly penetrates into the substrate sheet, and as a result, it is hardly wasted. It forms an oily film of its oily ingredient only in the necessary part of the skin of users.

In particular, the sheet of the invention is favorable to the top sheet of absorbent articles, and it surely protects the skin of babies subjected to diaper rash and the like.

While the invention has been described in detail and with reference to specific embodiments thereof, it will be apparent to one skilled in the art that various changes and modifications can be made therein without departing from the spirit and scope thereof.

What is claimed is:

1. A sheet, of which a surface to be in contact with a skin of a wearer has a mixture layer, the mixture layer consisting of:
   (a) an oily ingredient which is liquid or semi-solid at 25° C., and
   (b) an ester compound of dextrin with a fatty acid being present on said surface of the sheet in gel form for at least restricting penetration of said oily ingredient into said sheet and whereby serving as a carrier to retain said oily ingredient on said surface of the sheet.

2. The sheet as set forth in claim 1, wherein the fatty acid has from 12 to 22 carbon atoms.

3. The sheet as set forth in claim 1, wherein the mixture layer contains from 30 to 98% by weight of the oily ingredient and from 70 to 2% by weight of the ester compound.

4. The sheet as set forth in claim 1, wherein the ester compound is dextrin palmitate.

5. The sheet as set forth in claim 1, which is a non-woven fabric.

6. An absorbent article comprising:
   a top sheet;
   a back sheet; and
   an absorbent core sandwiched between said top sheet and said back sheet;
   said top sheet having a surface to be in contact with a skin of a wearer has a mixture layer, the mixture layer consisting of:
   (a) an oily ingredient which is liquid or semi-solid at 25° C., and
   (b) an ester compound of dextrin with a fatty acid being present on said surface of said top sheet in gel form for at least restricting penetration of said oily ingredient into said sheet and whereby serving as a carrier to retain said oily ingredient on said surface of said top sheet.

7. The sheet as set forth in claim 6, wherein the fatty acid has from 12 to 22 carbon atoms.

8. The sheet as set forth in claim 6, wherein the mixture layer contains from 30 to 98% by weight of the oily ingredient and from 70 to 2% by weight of the ester compound.

9. The sheet as set forth in claim 6, wherein the ester compound is dextrin palmitate.

10. The sheet as set forth in claim 6, which is a non-woven fabric.

11. An absorbent article comprising:
   a liquid-pervious top sheet;
   a back sheet;
   an absorbent core sandwiched between said top sheet and said back sheet; and
   a leak-preventing cuff for preventing side leakage and/or a leg cuff for preventing leakage around thighs of a wearer;
   a sheet forming said leak-preventing cuff and/or said leg cuff, having a surface to be in contact with a skin of wearer with a mixture layer consisting of:
   (a) an oily ingredient which is liquid or semi-solid at 25° C., and
   (b) an ester compound of dextrin with a fatty acid present on said surface of the sheet in gel form for at least restricting penetration of said oily ingredient into said sheet and whereby serving as a carrier to retain said oily ingredient on said surface of the sheet.

12. The sheet as set forth in claim 11, wherein the fatty acid has from 12 to 22 carbon atoms.

13. The sheet as set forth in claim 11, wherein the mixture layer contains from 30 to 98% by weight of the oily ingredient and from 70 to 2% by weight of the ester compound.

14. The sheet as set forth in claim 11, wherein the ester compound is dextrin palmitate.

15. The sheet as set forth in claim 11, wherein the sheet is a non-woven fabric.

16. The sheet as set forth in claim 1, wherein the sheet is for protecting wounds.

* * * * *